United States Patent
Mewes et al.

(10) Patent No.: US 10,828,006 B2
(45) Date of Patent: Nov. 10, 2020

(54) METHOD FOR CALIBRATING A MEDICAL IMAGING DEVICE, METHOD FOR PERFORMING A 2D-3D REGISTRATION, AND SYSTEM INCLUDING A MEDICAL IMAGING DEVICE

(71) Applicant: Siemens Healthcare GmbH, Erlangen (DE)

(72) Inventors: Philip Mewes, Nuremberg (DE); Gunter Müller, Heroldsberg (DE); Peter Fischer, Erlangen (DE); Holger Mönnich, Friedberg (DE); Martin Rube, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 25 days.

(21) Appl. No.: 16/231,509

(22) Filed: Dec. 22, 2018

(65) Prior Publication Data

US 2019/0192105 A1     Jun. 27, 2019

(30) Foreign Application Priority Data

Dec. 22, 2017   (EP) ..................................... 17210234

(51) Int. Cl.
*A61B 6/00*     (2006.01)
*A61B 90/00*     (2016.01)
(Continued)

(52) U.S. Cl.
CPC .............. *A61B 6/584* (2013.01); *A61B 6/032* (2013.01); *A61B 6/4441* (2013.01); *A61B 6/488* (2013.01);
(Continued)

(58) Field of Classification Search
CPC ......... A61B 6/584; A61B 90/37; A61B 6/032; A61B 6/4441; A61B 6/488; A61B 6/547;
(Continued)

(56) References Cited

U.S. PATENT DOCUMENTS

2007/0172033 A1   7/2007   Gorges
2010/0204562 A1*   8/2010   Gorges ................. A61B 6/0457
                                              600/407
(Continued)

FOREIGN PATENT DOCUMENTS

DE    102011005993 A1    9/2012
DE    102011114333 A1    3/2013
(Continued)

OTHER PUBLICATIONS

European Search Report for European Patent Application No. 172102345-1124 dated Jul. 10, 2018.
(Continued)

*Primary Examiner* — Courtney D Thomas
(74) *Attorney, Agent, or Firm* — Lempia Summerfield Katz LLC (57) ABSTRACT

A method for calibrating a medical imaging device in terms of an image acquisition geometry, a method for performing a two-dimensional-three-dimensional registration based on corresponding calibration data, and a corresponding system are provided. Multiple images of a phantom are acquired using the imaging device in different positions of the phantom. A corresponding motion of the phantom from one position to a respective next position is tracked by a tracking device to keep continuous track of a spatial relation between the phantom and the imaging device. The medical imaging device is then calibrated based on the acquired images, corresponding recorded poses of the imaging device, and the tracked motion of the phantom.

14 Claims, 2 Drawing Sheets

(51) Int. Cl.
*A61B 6/03* (2006.01)
*A61B 6/04* (2006.01)

(52) U.S. Cl.
CPC .............. *A61B 6/547* (2013.01); *A61B 6/583* (2013.01); *A61B 90/37* (2016.02); *A61B 6/0457* (2013.01); *A61B 6/469* (2013.01); *A61B 6/487* (2013.01); *A61B 6/5235* (2013.01); *A61B 2090/367* (2016.02); *A61B 2090/3762* (2016.02)

(58) Field of Classification Search
CPC .............. A61B 6/583; A61B 2090/367; A61B 2090/3762; A61B 6/469; A61B 6/487; A61B 6/5235
See application file for complete search history.

(56) References Cited

U.S. PATENT DOCUMENTS

| | | |
|---|---|---|
| 2010/0246778 A1 | 9/2010 | Heigl |
| 2011/0257508 A1 | 10/2011 | Feuerlein |
| 2014/0350387 A1 | 11/2014 | Siewerdsen |
| 2016/0278732 A1* | 9/2016 | Amiri .................. A61B 6/4441 |

FOREIGN PATENT DOCUMENTS

| | | |
|---|---|---|
| JP | 2012055393 A | 3/2012 |
| JP | 2015123317 A | 7/2015 |

OTHER PUBLICATIONS

Gorges, Sébastien, et al. "Model of a vascular C-arm for 3D augmented fluoroscopy in interventional radiology." International Conference on Medical Image Computing and Computer-Assisted Intervention. Springer, Berlin, Heidelberg, 2005. pp. 214-222.

OWIS Precision in Perfection, "Motorisierte Positioniersysteme", "Motorized Positioning Systems": http://www.owis.eu/produkte/motorisierte-positioniersysteme/produktgruppe/lineartische-1/productview/Main/ pp. 1-274, viewed Oct. 23, 2017.

* cited by examiner

FIG 1

METHOD FOR CALIBRATING A MEDICAL IMAGING DEVICE, METHOD FOR PERFORMING A 2D-3D REGISTRATION, AND SYSTEM INCLUDING A MEDICAL IMAGING DEVICE

This application claims the benefit of EP 17210234.5, filed on Dec. 22, 2017, which is hereby incorporated by reference in its entirety.

BACKGROUND

The present embodiments relate to calibrating a medical imaging device and performing a two-dimensional (2D)-three-dimensional (3D) registration.

Today, medical imaging techniques, such as computer tomography (CT), x-ray imaging, angiography, and others may provide detailed image data of a patient and may thereby contribute to a successful diagnosis and treatment of a patient. These same imaging techniques may, however, also expose the patient to significant radiation. It is therefore common practice to acquire a full 3D dataset of the patient or a region of interest (ROI) only once, typically before actual intervention or operation. During the intervention or operation, only 2D images of the patient or ROI are then acquired instead of multiple full 3D datasets to reduce exposure or stress of the patient. This approach does, however, bring with it the need for registering the 2D images with the previously taken 3D dataset or a common coordinate system or reference frame. This process is known as a 2D3D-registration.

A precise registration with reasonable effort is typically only possible for imaging positions for which the imaging device has previously been calibrated. For a calibrated imaging position, a precise relation between a respective current position or positioning state of the imaging device and the position or orientation in space of a 2D image acquired from that position or positioning state is known or predetermined through the corresponding preceding calibration.

Intermediate imaging positions situated between two calibrated imaging positions or imaging positions outside of a calibration space are typically interpolated or extrapolated from actual available calibration data acquired for a limited number of calibration positions or calibrated positions. This leads to a less-than-ideal overall precision in the 2D3D-registration and therefore, in a performance or usefulness of the medical imaging technique. Over a complete imaging space or maximum detection range of an imaging device, known calibration methods may, for example, result in an accuracy or precision on the order of 2 mm. This is or will be insufficient, for example, for navigated and/or robotic medical procedures.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a simple way of improving a performance of medical imaging techniques in practical applications is provided.

A method according to one or more of the present embodiments provides for calibrating a medical imaging device in terms of an image acquisition geometry of the medical imaging device. The method includes positioning an imaging phantom with predetermined geometrical features in a first position inside a maximum detection range of the imaging device. The maximum detection range in this sense is the complete volume of space that may be reached or imaged by the medical imaging device using a full range of motion or adjustability.

The imaging phantom may, for example, be an artificial object including an arrangement or a pattern of markers that may be imaged by the imaging device. Through these markers and/or, for example, a shape of the imaging phantom, a position and an orientation (e.g., a pose) may be unambiguously determined from image data or images of the imaging phantom taken or acquired with the imaging device. These markers may, for example, be metallic dots or spheres that may be arranged on a surface of the imaging phantom and/or integrated within the imaging phantom. The markers may be clearly detectable and distinguishable in x-ray images acquired with the medical imaging device.

As part of the method, at least one image of the phantom in the first position is acquired using the imaging device. A corresponding pose of the imaging device in which the at least one image is acquired is recorded or noted. The pose may be recorded or characterized absolutely or relatively (e.g., in terms of a corresponding control signal used to position the imaging device in that pose and/or in terms of a corresponding motion or movement of the imaging device). The latter may, for example, be detected or sensed using one or more positional or motion sensors. These sensors may, for example, be integrated into the imaging device (e.g., in or at respective joints of an articulated robotic arm of the imaging device).

The method further includes moving the phantom out of the first position and into at least one other position inside the maximum detection range (e.g., inside an imagable volume or a coverage range of the imaging device). At least one image of the phantom in the at least one other position is then acquired using the imaging device, and a corresponding pose of the imaging device is recorded or noted analogous to acquiring the at least one image of the phantom in the first position. Moving the phantom into at least one other position provides that the phantom may be continuously or discreetly moved into multiple positions. For each of these multiple positions, at least one respective image is then acquired or taken, and the corresponding pose of the imaging device is recorded.

While moving the phantom from the first position to the at least one other position and, if applicable, from each one of the other positions to a respective next one, the corresponding motion or movement of the phantom relative to the first position is tracked by a tracking device. Thereby, a continuous track of a spatial relation between the phantom and the imaging device is obtained or kept. In a further act of the method, the medical imaging device is then calibrated based on the acquired images, the corresponding recorded poses of the imaging device, and the tracked motion of the phantom. The imaging device is, in other words, calibrated by establishing a relation between the images of the phantom, a tracked motion of the phantom, and the recorded corresponding poses of the imaging device.

In known calibration methods, the phantom is not moved, since doing so would invalidate or corrupt respective calibration data acquired before and after moving the phantom. This is the case, because by moving the phantom, a spatial relation between the phantom or a position and the medical imaging device would be lost or become unknown. This provides that for a vast majority of the maximum detection range of the imaging device, no explicit and precise calibration data is typically available. Therefore, interpolation or extrapolation techniques are to be used when actually using the imaging device in practical applications. By tracking the motion of the phantom, however, one or more of the present embodiments enable acquisition of precise calibration data for a significantly larger portion of the maximum detection range of the imaging device. The present embodiments may, in other words, increase a size of a calibration space or calibrated space of or for the imaging device. This enables an improved precision or 2D-3D registrations and may thereby contribute to reducing exposure of the patient.

A typical imaging phantom may, for example, be of a cylindrical shape with a length of about 20 cm and a diameter of about 15 cm. While it is obviously possible to use a differently sized and/or shaped phantom, the size may not be arbitrarily increased. First, a larger phantom may also provide increased bending or deformation as well as thermal extension or contraction. This may again lead to a reduced precision. Second, regardless of a geometric precision or reliability of a larger phantom, it is typically not possible to cover or fill the whole maximum detection range of a medical imaging device with a single stationary phantom. This becomes obvious when considering a typical c-arm x-ray device, where the c-arm is attached to a multi jointed articulated robot arm while at the same time having a predetermined distance between an x-ray source and a corresponding detector at opposite ends of the c-arm. The maximum detection range may be as large as multiple cubic meters, and a distance between the source and detector mounted on the c-arm may be smaller than an extension of the maximum detection range in any direction.

Calibrating the medical imaging device may be done automatically using a control unit or a data processing device that may, for example, be part of the medical imaging device or a corresponding system, such as the system according to the present embodiments, which will be discussed in more detail below.

In other applications where spatial tracking of an object is to be provided, separate tracking systems, such as a laser tracking system or an optical tracking system, are typically employed. These tracking systems may, however, be prohibitively expensive and/or complex so that it is, for example, not feasible to provide multiple service technicians each with such a system for calibrating an existing medical imaging device installed at a customer or in a field location. As part of the present embodiments, multiple optional developments that may provide simple and affordable ways to achieve an improved calibration are therefore described. These embodiments, developments, or aspects are described below in further detail.

In a development, the motion of the phantom is tracked using the imaging device itself as at least part of the tracking device. The imaging device is, in other words, used to acquire multiple images of the phantom while the phantom is being moved into the at least one other position or a respective next position. In one embodiment, the imaging device is kept stationary while the multiple images are acquired (e.g., while the phantom is being moved). This approach or method may also be called "Fluoro-tracking". The motion of the phantom and therefore a relative position or relative positions of the phantom may be extracted or reconstructed from the multiple images acquired during the motion. This provides that the imaging device may be used analogous to a camera of a conventional external optical tracking system to track the phantom or movement of the phantom. Compared to using a conventional external tracking system, the method does, however, have the advantage of not requiring any additional setup or equipment, thereby enabling improved calibration of the medical imaging device with significantly reduced cost and complexity.

In a further development, to track the motion of the phantom using the imaging device, the phantom is at least partly permanently kept inside a respective current field of view of the imaging device while being moved. After the respective at least one image of the phantom in each position has been acquired, the imaging device is then moved corresponding to the respective last motion of the phantom before the phantom is again moved to a respective next one of the other positions. The phantom and the imaging device are, in other words, moved alternatingly so that at each point in time, at least one or the other is stationary (e.g., with respect to a rom coordinate system, the fixed coordinate system of the room in which the imaging device is installed). At all times, the part or portion of the phantom that is inside the field of view of the imaging device is to be large enough or is to contain enough markers or identifying features to unambiguously derive the respective current pose of the phantom. However, which exact part of the phantom is kept in the field of view may change over time. This provides that a part of the phantom in the field of view at a beginning of the motion of the phantom may be different from a part of the phantom that is in the field of view at an end of the motion.

The phantom may, for example, be moved only so far or so much that, depending on a respective pattern of markers, at least five or eight markers of the phantom are always visible in the respective current field of view of the imaging device. While the phantom is then being kept stationary in a respective current or new position, the imaging device is then moved to catch up with the moved phantom so that, for example, a larger part of the phantom or the whole phantom is again inside the field of view of the imaging device, or the phantom partly extends out of an opposite side of the field of view as compared to the beginning of the motion. This approach enables precise calibration for at least substantially the whole maximum detection range by alternatingly and sequentially moving the phantom and the imaging device through the maximum detection range while never losing knowledge or certainty about the spatial relation between the phantom and the imaging device.

In a development, the motion of the phantom is tracked by a camera attached to the phantom in a predetermined, fixed spatial relation to the phantom as at least part of the tracking device. The motion of the phantom is, in other words, tracked by a simultaneous localisation and mapping (SLAM) technique. Since the camera is rigidly attached to the phantom, the camera is also moved when the phantom is moved. The camera or a corresponding data processing device connected thereto via a data link may, for example, identify and track spatially fixed features of an external object, such as features of a wall, a ceiling, and/or a floor of a room in which the medical imaging device is installed. By processing image data capture or provided by the camera, a map of the current surroundings may be created, and the current position of the camera, and thereby the phantom, in the mapped surroundings may be determined. Advantageously, the camera may be a stereoscopic or 3D camera to allow for unambiguously determining and tracking the position of the phantom in three-dimensional space. This approach enables the proposed improved calibration with minimal cost and effort.

To further improve the tracking and calibration accuracy and/or precision, optical markers may be arranged around the medical imaging device in a field of view of the camera.

This may assist in the localisation and mapping, for example, if the surroundings lack readily identifiable geometric features and/or if lighting conditions are sub-optimal. It is, however, generally not necessary to place these optical markers in any particular or unique pattern, which again, advantageously reduces complexity and required effort.

In a development, to track the motion of the phantom as at least part of the tracking device, a mechanical ruler device is rigidly attached to a patient support on which the phantom is placed. The patient support may, for example, be part of the medical imaging device. The phantom is then moved along the ruler device into the at least one other position and, if applicable, into each respective next other position. The respective position and/or movement of the phantom is then recorded or measured with respect to the ruler device. The ruler device may, in other words, provide or act as a fixed yardstick to track and measure the motion and/or the respective position of the phantom with respect to the fixed room coordinate system in which the patient support may be stationary. Alternatively, it may also be possible to attach the mechanical ruler device to any other object that is stationary with respect to the room coordinate system. This approach may provide an easy to implement and potentially low-cost method for tracking the motion of the phantom and thereby enabling an increased size of the calibration space.

Tracking or measuring the position and/or motion of the phantom against or with respect to the ruler device may be accomplished manually or automatically. The ruler device may, for example, include multiple regularly spaced notches, while the phantom may include at least one corresponding protrusion. Arranging or placing the phantom so that the at least one protrusion fits into one of the multiple notches of the ruler device provides a simple and reliable way of advancing the position of the phantom in an easily trackable and reliably reproducible manner. This embodiment also avoids any negative optical parallax effects typically connected with manually taking a reading of a mechanical scale.

Many different concrete implementations of this approach are possible. For example, the protrusion of the phantom may be a spring-loaded ball that may be pushed completely inside of an outer perimeter of the phantom. This enables the phantom to be moved along the ruler device while maintaining permanent mechanical contact. In one embodiment, the ball or protrusion and, optionally, the corresponding recesses or notches of the ruler device may at least partly consist of a material, such as a metal or alloy, that is visible in images taken with the imaging device. This may provide an additional avenue for tracking the position and/or motion of the phantom by using the imaging device as part of the tracking device, as described above.

In any case, the ruler device may include one or more sensors for detecting when and where the protrusion of the phantom enters one of the notches or recesses of the ruler device. The ruler device may then provide corresponding data, for example, to a control unit configured to calibrate the imaging device. This may remove any human error in reading the current position of the phantom. Depending on an effort and a precision put into manufacturing the ruler device and the phantom, this approach may enable determining the respective current position of the phantom with a precision on the order of 0.1 mm or less.

In a development, to track the motion of the phantom, the phantom is moved by a linear stage. A linear stage enables precisely controlled motion along one axis and is also known as a translation stage or linear slide. Typical applications for a linear stage may, for example, be found in optics lab stages. Applied to the presently described method, the linear stage may, for example, be placed upon or mounted to a patient support. The phantom may be placed on top of the linear stage and thus may be moved as a payload of the linear stage. Non-moving parts of the linear stage may remain stationary with respect to the room coordinate system and/or with respect to the patient support on which the non-moving parts of the linear stage may be placed. Operating the linear stage to move the phantom may be done manually. In one embodiment, however, the linear stage may be motorized and, for example, electronically controlled (e.g., by the control unit). A linear stage provides a simple to implement or apply, precise, and relatively inexpensive way for moving the phantom in a precise, trackable, and controllable manner to extend the size of the calibration space (e.g., a number of and volume covered by calibrated imaging positions). Linear stages are available with travels of, for example, about 400 mm, which may be enough to significantly increase the calibration space as compared to conventional methods where the phantom remains stationary.

In a development, as at least part of the tracking device, a laser distance meter or laser rangefinder is rigidly attached to the phantom and/or a patient support on which the phantom is placed. To track the motion of the phantom, a distance to any positionally fixed or stable external reference object is measured using the laser distance meter (e.g., while the phantom is being moved). The distance may, for example, be measured from the laser distance meter to a wall, ceiling, and/or floor of a surrounding room in which the imaging device is installed. Alternatively or additionally, the distance between the laser distance meter and a non-moving or stationary part of the imaging device, such as a foot or base, may be measured to track the motion of the phantom. The laser distance meter may include multiple laser beams that extend or radiate in different directions. This may allow for tracking the motion of the phantom in two or three dimensions. In one embodiment, the laser distance meter and/or an attachment of the laser distance meter to the phantom may be adjustable to orient the laser distance meter or a direction of a laser beam or laser beams of the laser distance meter. This may allow for improved flexibility, so that the described setup may be used to track the motion of the phantom in different settings or surroundings. At least one laser beam of the laser distance meter may be pointed in or parallel to a direction in which the phantom is being moved. Additional laser beams and/or laser distance meters may, for example, be pointed at least approximately perpendicular to this direction.

A change in distance between the laser distance meter, and therefore the phantom, and the reference object, which remains stationary in the coordinate system in which the phantom is moving, relates to the movement of the phantom and may thus be used or processed to describe or characterize the movement or motion of the phantom. Using the laser distance meter in this manner may allow for tracking the motion and relative position of the phantom with, for example, sub-millimetre accuracy, while at the same time being easy and simple to transport and to implement, and also being relatively inexpensive.

In a further development, the phantom is placed, directly or indirectly, on the patient support. To move the phantom, the patient support itself is then moved. An indirect placement of the phantom on the patient support may, for example, provide that the phantom is placed upon another device or implement, such as the linear stage, which is placed upon the patient support.

The patient support may be part of the medical imaging device and may be designed to be moved or adjusted. Using the patient support to move the phantom may allow for covering a majority of a space or volume in which any patient would be positioned for any practical application of the imaging device. Using the patient support to move the phantom also offers the advantage that no additional motor or movement device is to be provided, which may reduce complexity, cost, and effort required for performing the calibration of the imaging device. Typical movable or adjustable patient supports available today do, however, not offer the required precision in terms of distance, direction, and repeatability or reproducibility of the motion. Combining the use of the motor or a drive mechanism of the patient support already in place as part of the imaging device and an additional device, such as the camera and/or the laser distance meter, to track the motion with the required precision, offers an optimum efficiency and effectiveness in tracking the motion of the phantom and calibrating the medical imaging device (e.g., in terms of cost, complexity, and implementation effort).

Mentions of the patient support made in different contexts throughout the description may refer to one and the same patient support. The same may also be applied to any other device, part, or method, respectively.

Another aspect is a method for performing a 2D-3D registration between at least one 2D-image acquired using a medical imaging device and at least one 3D-dataset previously acquired using the same medical imaging device. The medical imaging device may, for example, be the same imaging device mentioned above with respect to the method for calibrating the medical imaging device. The 3D dataset of an object (e.g., of a patient) is acquired. Then, a 2D-image of the object or a patient is acquired. The 2D-image is then registered with a coordinate system of the 3D-dataset in dependence on calibration data for the medical imaging device obtained by a method for calibrating the medical imaging device in accordance with the present embodiments. In other words, at least one development of the method for calibrating the medical imaging device described herein may be implemented as part of a larger or more elaborate procedure that also includes performing the 2D-3D registration, for example, as part of a medical diagnostic and/or interventional procedure. This is advantageous, since it is an advantage of the described calibration method to enable a more precise and reliable 2D3D-registration.

Another aspect is a system including at least a medical imaging device and a control unit. The system further includes a tracking device for tracking a motion of an imaging phantom with predetermined geometrical features inside a maximum detection range of the imaging device. The system is configured for calibrating the imaging device in terms of an image acquisition geometry by a method for calibrating the medical imaging device in accordance with the present embodiments. The system is alternatively or additionally configured to automatically perform a 2D-3D registration by a corresponding method in accordance with the present invention. The control unit may include a processing unit (e.g., a processor) as well as a data storage device (e.g., a memory). The data storage device may contain program code that implements any or all acts of the above-mentioned methods and is configured to be executed by the processing unit of the control unit.

The embodiments and developments described herein for at least one aspect (e.g., for the method for calibrating the medical image device, the method for performing the 2D3D-registration, and the system), as well as the corresponding advantages may be applied to any and all aspects. For example, multiple of the different methods or implementations for tracking the motion of the phantom may be used or applied (e.g., implemented) simultaneously. Correspondingly, the system according to the present embodiments may include the necessary devices (e.g., processors) for executing one or more of these methods simultaneously.

Further advantages, features, and details of the present invention derive from the following description of embodiments of the present invention as well as from the drawings pertaining to the present invention. The features and feature combinations previously mentioned in the description as well as the features and feature combinations mentioned in the following description of the figures and/or shown in the figures alone may be employed not only in the respectively indicated combination but also in other combinations or taken alone without leaving the scope of the present invention.

DETAILED DESCRIPTION

Figure 1:
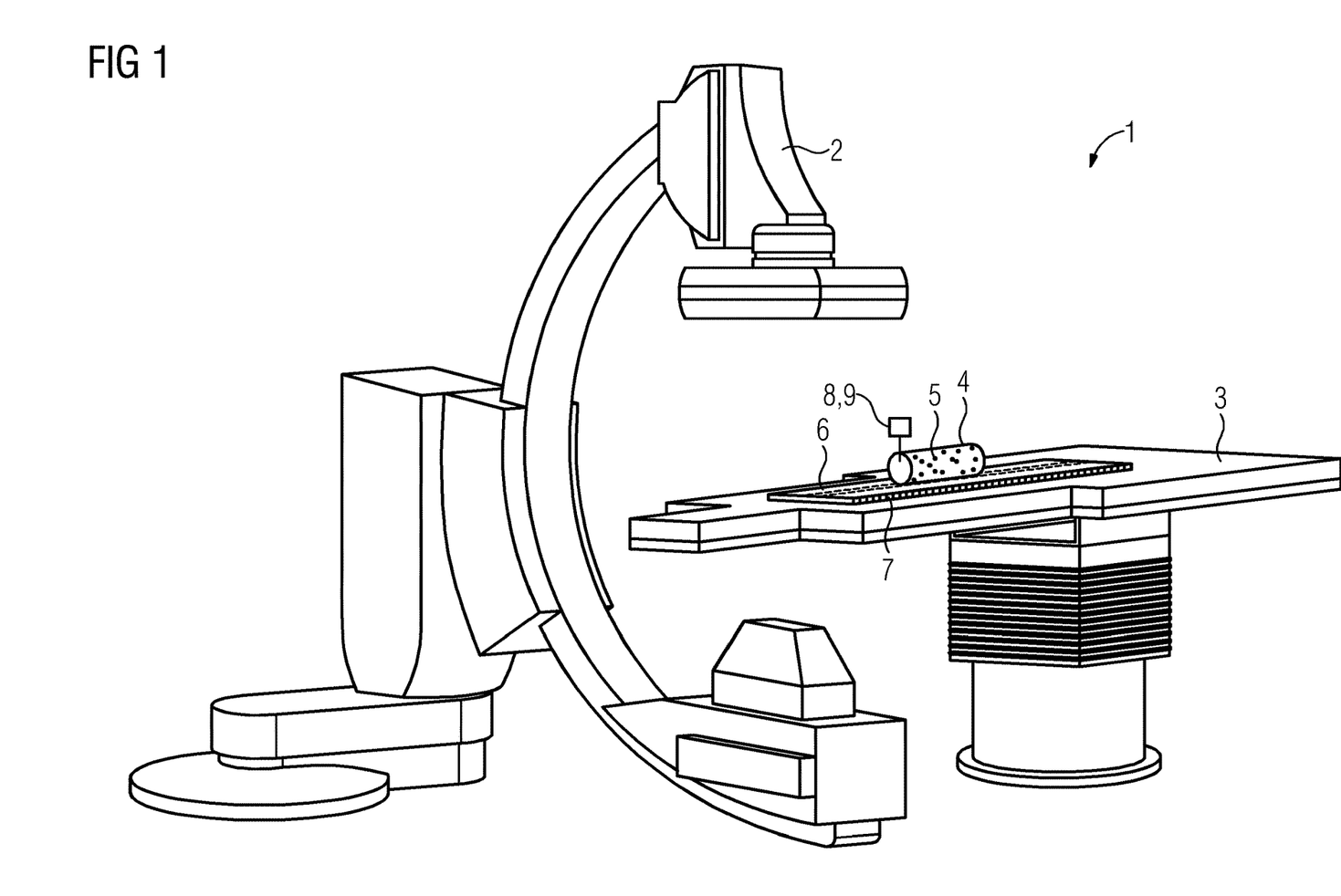
FIG. 1 shows a perspective view of one embodiment of a system including a c-arm x-ray device, a patient support, and a tracking device for calibrating the x-ray device.

FIG. 1 schematically shows one embodiment of a system 1 including a medical imaging device 2 that, in the present example, is a c-arm x-ray device. The system 1 or the imaging device 2, respectively, further includes a patient support 3 that is adjustable. Placed on the patient support 2 is an imaging phantom 4 in the form of a cylindrical object including multiple x-ray-visible markers 5 arranged in a pattern to uniquely or unambiguously identify a pose of the phantom 4 in or from x-ray images or corresponding image data obtained using the imaging device 2. Because a geometry of the phantom 4 and the pattern of markers 5 is predetermined and known, the phantom 4 may be used to calibrate the imaging device 2. A corresponding method for calibrating the imaging device 2 will be described with reference to FIG. 2, which schematically shows an exemplary flow chart 10, illustrating multiple process acts.

Figure 2:
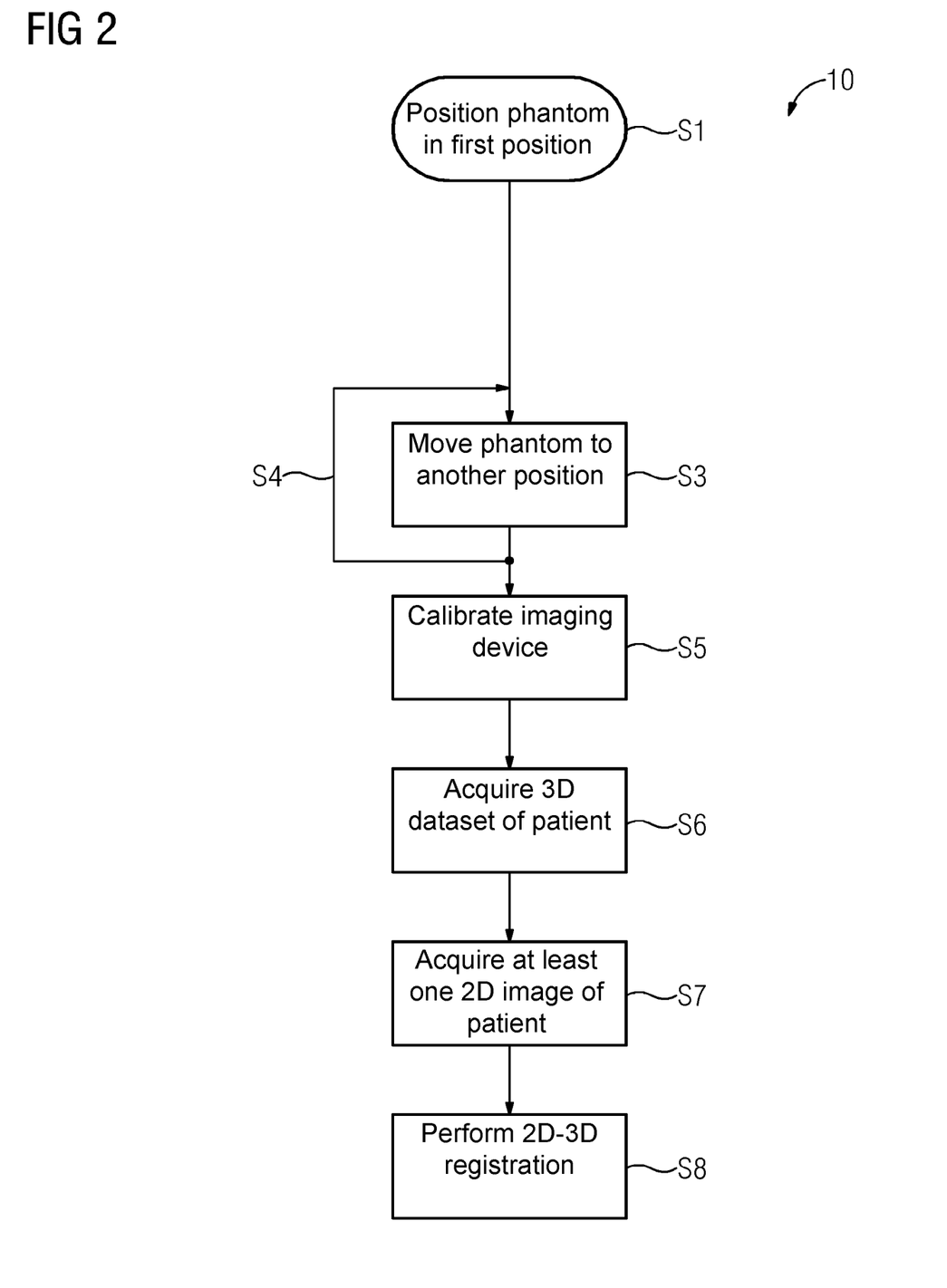
FIG. 2 shows an exemplary flow chart of one embodiment of a method for calibrating a medical imaging device, such as the c-arm x-ray device shown in FIG. 1, and performing a 2D-3D registration based on corresponding calibration data.

The method starts with a process act S1, where the phantom 4 is positioned in a first position inside a maximum detection range of the imaging device 2 (e.g., on the patient support 3). While the phantom 4 is arranged in this first position, at least one image of the phantom 4 is taken or acquired using the imaging device 4. Also, a corresponding pose of the imaging device 2 is recorded. Multiple images of the phantom 4 or parts thereof may be acquired from different angles or perspectives. This provides that while the phantom 4 remains in the first position, the imaging device 2 may be moved to different imaging positions around the phantom 4. In this case, the corresponding pose of the imaging device 2 is recorded for each of the multiple acquired images.

In a process act S3, the phantom 4 is moved out of the first position and into another position inside the maximum detection range of the imaging device 2. While the phantom 4 is being moved, the imaging device 2 may remain stationary. Analogous to the first position, at least one image of the phantom 4 or a part thereof is then taken in the new other position of the phantom 4 using the imaging device 2. Corresponding poses of the imaging device 2 are recorded for each image. This process of moving the phantom 4 into a new position and then taking at least one respective image may be repeated multiple times in a process act S4, which is correspondingly indicated in FIG. 2 as a loop.

During the process acts S3 and S4, the motion or movement of the phantom 4 is tracked relative to the first and/or a respective previous position. Moving the phantom 4 and tracking a movement or motion including a respective current position of the phantom 4 may be achieved in one or more of multiple different ways.

First, the patient support 3 may be adjusted in terms of a position and orientation to move the phantom 4 placed thereon through at least part of the maximum detection range of the imaging device 2. Presently, the phantom 4 is placed upon a linear stage 6, which itself is attached to or placed upon the patient support 3. Alternatively or in addition to moving or adjusting the patient support 3, the phantom 4 may be moved by the linear stage 6. It may also be possible to use multiple linear stages 6 in combination to move the phantom 4 in different directions or along different axes independently. As part of the linear stage 6 or as a separate device, a ruler device 7 is provided. The ruler device 7 may mechanically track the motion and/or a respective current position of the phantom 4 when the phantom 4 is moved along the ruler device 7. For this purpose, the ruler device 7 may include multiple notches or recesses. The phantom 4 may correspondingly include a protrusion that may fit or snap into each one of the notches or recesses of the ruler device 7, thereby giving a precise location for the phantom 4, at least with respect to the ruler device 7.

When using the linear stage 6 and/or the ruler device 7, these may track the motion and position of the phantom 4 as part of function. Alternatively or additionally, for example, when moving the phantom 4 by adjusting the patient support 3, one or more different ways of tracking the motion and position of the phantom 4 may be employed.

For example, the imaging device 2 itself may be used to track the motion of the phantom 4. For this method, the imaging device 2 may be kept stationary while the phantom 4 is being moved from one position to the next. Then, while the phantom 4 is kept stationary in a respective new or current position, the imaging device 2 is moved correspondingly, typically in the same direction as the respective foregoing motion of the phantom 4. This stepwise alternating movement of the phantom 4 and the imaging device 2 may be repeated multiple times. During this process, the phantom 4 is at least partly kept inside a respective current field of view of the imaging device 2. For example, a portion of the phantom 4 including at least a part of the pattern of markers 5 is kept inside the field of view, where the part of the pattern of markers 5 is sufficient to uniquely and unambiguously derive the respective pose of the phantom 4 from corresponding images or image data acquired using the imaging device 2.

As an additional or alternative way for tracking the motion and position of the phantom 4, presently a camera 8 and/or a laser distance meter 9 is or are attached to the phantom 4. The camera 8 may be used to image and track features of a surrounding room in which the imaging device 2 is presently installed and/or stationary features of the imaging device 2 itself and/or the patient support 3. A SLAM-technique may then be used for building a map of the surroundings and to determine and track the position of the phantom 4 with respect to these surroundings. The laser distance meter 9 may be used to continuously measure a distance between the laser distance meter 9 and, for example, a wall of the surrounding room. By assuming that the wall remains stationary and analyzing any changes in the measured distance, the relative motion of the phantom 4 may be determined.

Multiple of the described methods may be used in conjunction or combination. This may improve an accuracy of the motion and/or position tracking. Results from different methods may also be used to provide redundancy as a safety measure against failure of a method or component. The results of multiple different methods may also be used to verify or plausibilize the results of one or more respective other methods.

In a process act S5, the imaging device 2 is then calibrated based on the acquired results or calibration data (e.g., based on the acquired images), the corresponding recorded poses of the imaging device 2, and the tracked motion of the phantom 4 and/or results derived therefrom.

For a practical application, a 3D-dataset of a patient is then acquired using the medical imaging device 2 in a process act S6.

In a process act S7, which may take place, for example, several hours or days after process act S6, at least one 2D-image (e.g., multiple 2D-images) of the same patient are acquired using the imaging device 2, for example, as part of a medical procedure. For example, if the patient and/or the imaging device 2 is moved during this procedure, a 2D-3D registration between the respective currently acquired 2D images and the 3D dataset previously acquired in process act S6 is necessary to retain data consistency and provide the medical personnel with needed information or insight about the state of the patient and/or the procedure without subjecting the patient to unnecessary high doses of radiation, which would result from acquiring another full 3D-dataset during the medical procedure.

The 2D-3D registration using the previously acquired calibration data for the imaging device 2 is then performed in a process act S8.

In summary, the presently described examples illustrate how a calibration of a medical imaging device, such as the imaging device 2, may be improved by extending a calibration space through relatively simple and inexpensive ways by tracking a motion of the phantom 2 during the calibration process to accurately map a larger portion the maximum detection range of the respective medical imaging device. The improved calibration may then be used to perform a 2D-3D registration with improved accuracy and reliability, since because of the increased calibration space, no or less interpolation and/or extrapolation is required.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for calibrating a medical imaging device in terms of an image acquisition geometry, the method comprising:
positioning an imaging phantom with predetermined geometrical features in a first position inside a maximum detection range of the medical imaging device;
acquiring at least one image of the imaging phantom in the first position using the medical imaging device and recording a corresponding pose of a C-arm of the medical imaging device;
moving the imaging phantom out of the first position and into at least one other position inside the maximum detection range of the medical imaging device, and acquiring at least one image of the imaging phantom in the at least one other position using the medical imaging device and recording a corresponding pose of the C-arm of the medical imaging device;
while moving the imaging phantom, tracking, by a tracking device, a motion of the imaging phantom relative to the first position, thereby keeping continuous track of a spatial relation between the imaging phantom and the medical imaging device; and
calibrating the medical imaging device based on the acquired images, the corresponding recorded poses of the C-arm of the medical imaging device, and the tracked motion of the imaging phantom.

2. The method of claim 1, wherein the motion of the imaging phantom is tracked using the medical imaging device itself as at least part of the tracking device.

3. The method of claim 2, wherein tracking the motion of the imaging phantom using the imaging device comprises:
keeping the imaging phantom at least partly permanently inside a respective current field of view of the medical imaging device while being moved; and
after the respective at least one image of the imaging phantom in each position has been acquired, moving the medical imaging device with a movement corresponding to the respective last motion of the imaging phantom before the imaging phantom is again moved to a next one of the other positions.

4. The method of claim 1, wherein the motion of the imaging phantom is tracked by a camera attached to the imaging phantom in a predetermined, fixed spatial relation to the imaging phantom as at least part of the tracking device.

5. The method of claim 1, wherein tracking the motion of the imaging phantom comprises:
moving the imaging phantom along a mechanical ruler device into the at least one other position, the mechanical ruler device being rigidly attached to a patient support on which the imaging phantom is placed and being at least part of the tracking device; and
recording the position of the imaging phantom with respect to the mechanical ruler device.

6. The method of claim 1, wherein tracking the motion of the imaging phantom comprises moving, by a linear stage, the imaging phantom.

7. The method of claim 1, wherein a laser distance meter is rigidly attached to the imaging phantom, a patient support on which the imaging phantom is placed, or the imaging phantom and the patient support, and
wherein tracking the motion of the imaging phantom comprises measuring a distance to any positionally fixed external reference object using the laser distance meter while the imaging phantom is being moved.

8. The method of claim 4, wherein the imaging phantom is placed on a patient support, and
wherein moving the imaging phantom comprises moving the patient support.

9. A method for performing a two-dimensional (2D)-three-dimensional (3D) registration between at least one 2D image acquired using a medical imaging device and at least one 3D dataset previously acquired using the same medical imaging device, the method comprising:
acquiring the at least one 3D dataset of an object;
acquiring the at least one 2D image of the object; and
registering the at least one 2D image with a coordinate system of the at least one 3D dataset in dependence on calibration data for the medical imaging device obtained by calibrating the medical imaging device, the calibrating of the medical imaging device comprising:
positioning an imaging phantom with predetermined geometrical features in a first position inside a maximum detection range of the medical imaging device;
acquiring at least one image of the imaging phantom in the first position using the medical imaging device and recording a corresponding pose of a C-arm of the medical imaging device;
moving the imaging phantom out of the first position and into at least one other position inside the maximum detection range of the medical imaging device, and acquiring at least one image of the imaging phantom in the at least one other position using the medical imaging device and recording a corresponding pose of the C-arm of the medical imaging device;
while moving the imaging phantom, tracking, by a tracking device, a motion of the imaging phantom relative to the first position, thereby keeping continuous track of a spatial relation between the imaging phantom and the medical imaging device; and
calibrating the medical imaging device based on the acquired images, the corresponding recorded poses of the C-arm of the medical imaging device, and the tracked motion of the imaging phantom.

10. The method of claim 9, wherein the object is a patient.

11. A system comprising:
a medical imaging device;
a controller; and
a tracking device configured to track a motion of an imaging phantom with predetermined geometrical features inside a maximum detection range of the medical imaging device, wherein the system is configured to:
calibrate the medical imaging device in terms of an image acquisition geometry, the calibration comprising:
position the imaging phantom with the predetermined geometrical features in a first position inside the maximum detection range of the medical imaging device;
acquisition of at least one image of the imaging phantom in the first position using the medical imaging device and recordation of a corresponding pose of a C-arm of the medical imaging device;
movement of the imaging phantom out of the first position and into at least one other position inside the maximum detection range of the medical imaging device, and acquisition of at least one image of the imaging phantom in the at least one other position using the medical imaging device and recordation of a corresponding pose of the C-arm of the medical imaging device;

during movement of the imaging phantom, track, by a tracking device, a motion of the imaging phantom relative to the first position, thereby keeping continuous track of a spatial relation between the imaging phantom and the medical imaging device; and calibration of the medical imaging device based on the acquired images, the corresponding recorded poses of the C-arm of the medical imaging device, and the tracked motion of the imaging phantom; and automatically perform a two-dimensional (2D)-three-dimensional (3D) registration between at least one 2D image acquired using the medical imaging device and at least one 3D dataset previously acquired using the same medical imaging device, the automatic performance of the 2D-3D registration comprising:

acquisition of the at least one 3D dataset of an object;

acquisition of the at least one 2D image of the object; and registration of the at least one 2D image with a coordinate system of the at least one 3D dataset in dependence on calibration data for the medical imaging device obtained by the calibration of the medical imaging device; or a combination thereof.

12. The system of claim 11, wherein the system is configured to calibrate the medical imaging device in terms of the image acquisition geometry.

13. The system of claim 12, wherein the system is configured to automatically perform the 2D-3D registration.

14. The system of claim 11, wherein the system is configured to automatically perform the 2D-3D registration.

* * * * *